US012642845B2

(12) United States Patent (10) Patent No.: US 12,642,845 B2
Chen et al. (45) Date of Patent: Jun. 2, 2026

(54) PD1-BASED VACCINATION COMPOSITION AND METHODS THEREOF

(71) Applicant: VERSITECH LIMITED, Hong Kong (CN)

(72) Inventors: Zhiwei Chen, Hong Kong (CN); Zhiwu Tan, Hong Kong (CN)

(73) Assignee: Versitech Limited, Hong Kong (CN)

( * ) Notice: Subject to any disclaimer, the term of this patent is extended or adjusted under 35 U.S.C. 154(b) by 780 days.

(21) Appl. No.: 17/904,646

(22) PCT Filed: Feb. 4, 2021

(86) PCT No.: PCT/CN2021/075254
§ 371 (c)(1),
(2) Date: Aug. 19, 2022

(87) PCT Pub. No.: WO2021/164563
PCT Pub. Date: Aug. 26, 2021

(65) Prior Publication Data
US 2023/0097958 A1 Mar. 30, 2023

Related U.S. Application Data

(60) Provisional application No. 62/978,911, filed on Feb. 20, 2020.

(51) Int. Cl.
*C12N 15/00* (2006.01)
*A61K 39/00* (2006.01)
*A61K 39/395* (2006.01)
*A61P 35/00* (2006.01)

(52) U.S. Cl.
CPC .. *A61K 39/001152* (2018.08); *A61K 39/0011* (2013.01); *A61K 39/39541* (2013.01); *A61P 35/00* (2018.01); *A61K 2039/505* (2013.01); *A61K 2039/5158* (2013.01); *A61K 2039/53* (2013.01); *A61K 2039/545* (2013.01); *A61K 2039/80* (2018.08)

(58) Field of Classification Search
CPC ........ A61K 39/001152; A61K 39/0011; A61K 39/39541; A61K 2039/505; A61K 2039/53; A61K 2039/55516; A61P 35/00
See application file for complete search history.

(56) References Cited

U.S. PATENT DOCUMENTS

2019/0022204 A1* 1/2019 Lyerly .................... A61P 35/00

FOREIGN PATENT DOCUMENTS

| CN | 101501055 | A | 8/2009 |
| CN | 107109491 | A | 8/2017 |
| KR | 20200018351 | A | 2/2020 |
| WO | 2017150698 | A1 | 9/2017 |

OTHER PUBLICATIONS

Tan et al (Molecular therapy: Oncolytics 16: p. 302-317, published on Feb. 8, 2020, IDS item #8 dated Jan. 11, 2023 (Year: 2020).*
Khan et al (Frontiers in Immunology, vol. 11, p. 1-16, Nov. 19, 2020 (Year: 2020).*
Zhao et al Oncotarget 8:20380-93, 2017 (Year: 2017).*
Tan Z, Zhou J, Cheung AK, Yu Z, Cheung KW, Liang J, et al. Vaccine-elicited CD8+ T cells cure mesothelioma by overcoming tumor-induced immunosuppressive environment. Cancer Res. 2014;74(21):6010-21.
Ardiani A, Gameiro SR, Palena C, Hamilton DH, Kwilas A, King TH, et al. Vaccine-mediated immunotherapy directed against a transcription factor driving the metastatic process. Cancer Res. 2014;74(7):1945-57.
Malamas AS, Hammond SA, Schlom J, Hodge JW. Combination therapy with an OX40L fusion protein and a vaccine targeting the transcription factor twist inhibits metastasis in a murine model of breast cancer. Oncotarget. 2017;8(53):90825-41.
Zhou J, Cheung AK, Tan Z, Wang H, Yu W, Du Y, et al. PD1-based DNA vaccine amplifies HIV-1 GAG-specific CD8+ T cells in mice. J Clin Invest. 2013;123(6):2629-42.
Kwilas AR, Ardiani A, Dirmeier U, Wottawah C, Schlom J, Hodge JW. A poxviral-based cancer vaccine the transcription factor twist inhibits primary tumor growth and metastases in a model of metastatic breast cancer and Improves survival in a spontaneous prostate cancer model. Oncotarget. 2015;6(29):28194-210.
Field CS, Hunn MK, Ferguson PM, Ruedl C, Ancelet LR, Hermans IF. Blocking CTLA-4 while priming with a whole cell vaccine reshapes the oligoclonal T cell infiltrate and eradicates tumors in an orthotopic glioma model. Oncoimmunology. 2017;7(1):e1376154.
Ribas A, Comin-Anduix B, Chmielowski B, Jalil J, de la Rocha P, McCannel TA, et al. Dendritic cell vaccination combined with CTLA4 blockade in patients with metastatic melanoma. Clin Cancer Res. 2009;15(19):6267-76.
Tan, Z.W et al., "Antimesothelioma Immunotherapy by CTLA-4 Blockade Depends on Active PD1-Based TWIST1 Vaccination", Molecular Therapy-Oncolytics, vol. 16, Feb. 8, 2020 (Feb. 8, 2020).
Li, Y., "Energy Metabolism Reprogramming Induced By Twist In Breast Cancer Cells And Their Underlying Mechanisms", China Doctoral Dissertations Full-Text Database, No. 10, Oct. 15, 2016 (Oct. 15, 2016).

* cited by examiner

*Primary Examiner* — Lei Yao
(74) *Attorney, Agent, or Firm* — Leason Ellis LLP

(57) ABSTRACT

Provided herein is DNA vaccine and composition comprising PD1-based TWIST1. Also provided is a method for inducing TWIST1-specific T cell response by administering a PD1-based TWIST1 vaccine. Also provided is a method for inducing TWIST1-specific T cell response by administering a PD1-based TWIST1 vaccine and an immune checkpoint inhibitor.

14 Claims, 9 Drawing Sheets

Figure 1:
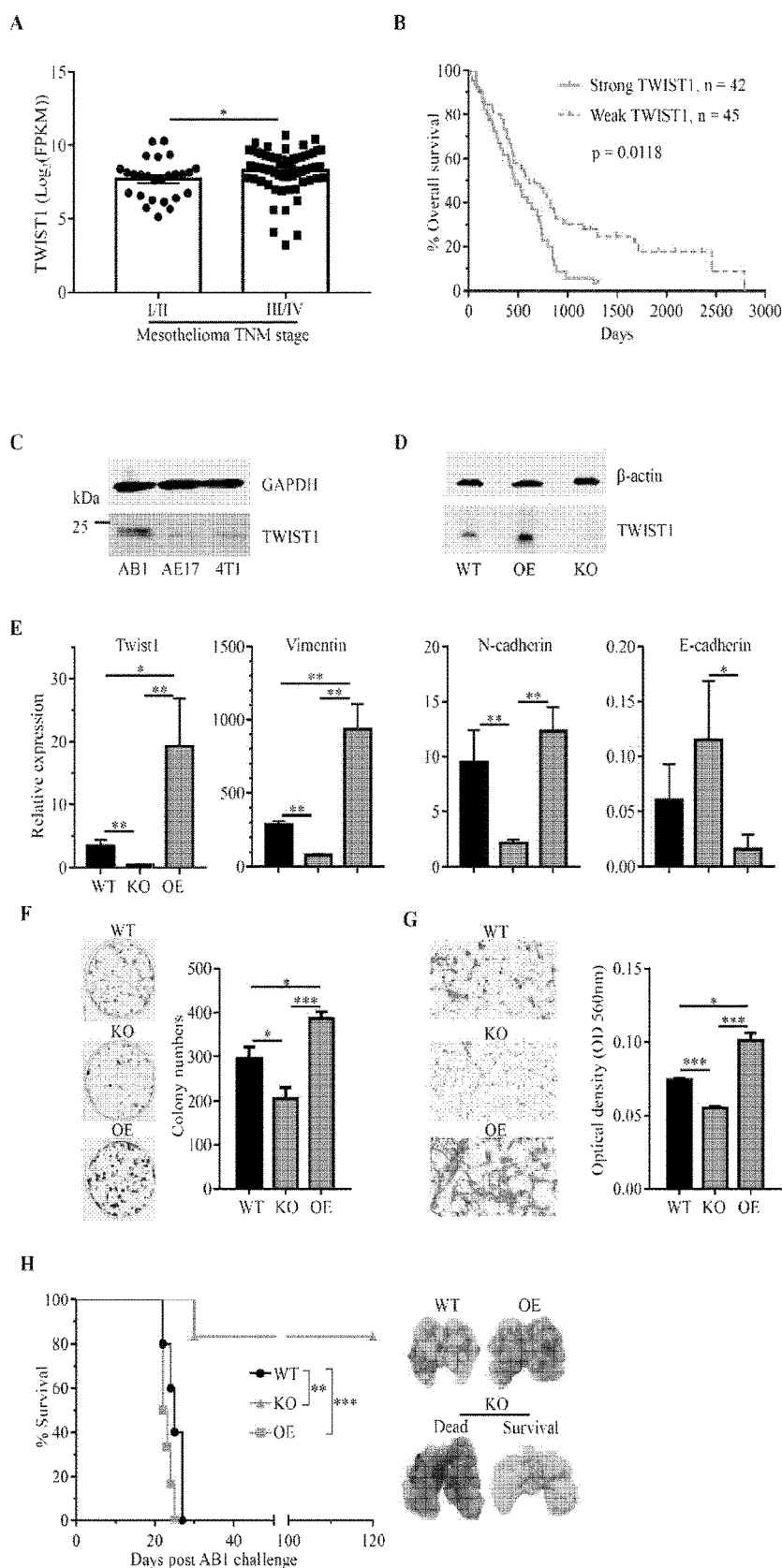

Specification includes a Sequence Listing.

FIG. 3

A pVAX.1 vector sTWIST1 sPD1-TWIST1

B

A

- pVAX.1 + α-CTLA-4
- sPD1-TWIST1 + isotype
- sPD1-TWIST1 + α-CTLA-4
- CD4 .sPD1-TWIST1 + α-CTLA-4
- CD8 .sPD1-TWIST1 + α-CTLA-4

B

| NO. | sequence |
|-----|----------|
| 37 | DKLSKIQTLKLAARY |
| 38 | KIQTLKLAARYIDFL |
| 39 | LKLAARYIDFLYQVL |
| 40 | ARYIDFLYQVLQSDE |
| 41 | DFLYQVLQSDELDSK |
| 42 | QVLQSDELDSKMASC |

```
                         SEQUENCE LISTING

<160> NUMBER OF SEQ ID NOS: 29

<210> SEQ ID NO 1
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Lys Leu Ser Lys Ile Gln Thr Leu Lys Leu Ala Ala Arg Tyr Ile
1               5                   10                  15

Asp Phe Leu Tyr Gln Val Leu
            20

<210> SEQ ID NO 2
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Arg Tyr Ile Asp Phe Leu Tyr Gln Val Leu Gln Ser Asp Glu Leu
1               5                   10                  15

Asp Ser Lys Met Ala Ser Cys
            20

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Tyr Gln Val Leu Gln Ser Asp Glu Leu
1               5                   10

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Lys Leu Ser Lys Ile Gln Thr Leu Lys Leu Ala Ala Arg Tyr Ile
1               5                   10                  15

Asp Phe Leu
```

-continued

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ttgctcaggc tgtcgtcggc                                                       20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
agctacgcct tctccgtctg                                                       20

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctccttctct ggaaacaatg aca                                                   23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tgacctctct gaggctgcca acc                                                   23

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ttccatctca cgcatctggc gctc                                                  24

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aaagagcgcc aagccaagca gc                                                    22
```

-continued

```
<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgcggatcgg actgggtact gtg                                                     23

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
acaccgatgg tgagggtaca cagg                                                    24

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gccgccacac acagcatagt ctc                                                     23

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cctgtcctgc attgccatga t                                                       21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cccactggca aactacaccc                                                         20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gattccccaa gtggcatata ca                                                      22

<210> SEQ ID NO 17
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tggagactcc ttctgagcta gtg                                                23

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tgctaaggca gttttggcta agtct                                              25

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aaaaacagtg gtggggaaca tg                                                 22

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ggcatgggtc agaaggatt                                                     19

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggggtgttga aggtctcaaa                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggtcctcagt gtagcccaag                                                    20

<210> SEQ ID NO 23
<211> LENGTH: 20
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aatgtgtccg tcgtggatct                                                    20

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Lys Leu Ser Lys Ile Gln Thr Leu Lys Leu Ala Ala Arg Tyr
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Ile Gln Thr Leu Lys Leu Ala Ala Arg Tyr Ile Asp Phe Leu
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Lys Leu Ala Ala Arg Tyr Ile Asp Phe Leu Tyr Gln Val Leu
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Arg Tyr Ile Asp Phe Leu Tyr Gln Val Leu Gln Ser Asp Glu
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Phe Leu Tyr Gln Val Leu Gln Ser Asp Glu Leu Asp Ser Lys
1               5                   10                  15
```

-continued

```
<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Val Leu Gln Ser Asp Glu Leu Asp Ser Lys Met Ala Ser Cys
1               5                   10                  15
```

PD1-BASED VACCINATION COMPOSITION AND METHODS THEREOF

This application is a U.S. National Stage Application under 35 U.S.C. § 371 of International Patent Application No. PCT/CN2021/075254 filed Feb. 4, 2021, which claims the benefit of U.S. Provisional Patent Application No. 62/978,911 filed on Feb. 20, 2020, both of which are incorporated by reference in their entireties. The International Application was published on Aug. 26, 2021, as International Publication No. WO/2021/164563.

SEQUENCE LISTING

The instant application contains a Sequence Listing which has been submitted electronically in ASCII format and is hereby incorporated by reference in its entirety. Said ASCII copy, created on Nov. 25, 2025, is named 10030_008216-US1_SL.txt and is 7,676 bytes in size.

1. FIELD

The present disclosure is in the field of cancer immunotherapy, cancer vaccine, compositions and methods thereof.

2. BACKGROUND

Malignant mesothelioma is a lethal type of cancer linked to historical exposure to airborne asbestos that typically arises from the pleura. The incidence and mortality of mesothelioma continue to rise in developing countries primarily (1). Treating malignant mesothelioma is challenging because the majority of patients (>75%) experienced relapse even after multimodality treatment (combined surgery, chemotherapy, and/or radiotherapy) (2). Chemotherapy with pemetrexed plus cisplatin has been the only approved regimen for more than a decade, but this approach only achieved modest benefits at best and many patients are unfit for such treatment (3). Although antibodies targeting immune checkpoint molecules, such as cytotoxic T lymphocyte associated protein 4 (CTLA-4), programmed cell death protein 1 (PD1) and programmed death-ligand 1 (PD-L1), have improved therapeutic efficacy in certain cancers, their effects are unsatisfactory in patients with mesothelioma (4). In particular, the first randomized phase III trial against mesothelioma using anti-CTLA-4 antibody failed to meet its primary end point of improved overall survival (5, 6). PD1 and PD-L1 checkpoint blockade antibodies have been shown some promising results in treating advanced mesothelioma in phase I/II trials, yet the overall responsive rate is below 30% (7, 8). In order to enhance the efficacy of existing immunotherapy, we speculate that it is still needed to elicit antitumor responses through active vaccination in mesothelioma patients.

Cancer vaccines involve boosting and proper activation of patients' own immune surveillance (9, 10). Despite extensive efforts, however, therapeutic cancer vaccines still show few favorable outcomes in the establishment of clinical responses in advanced cancer patients, largely owning to the limited immunogenicity of tumor antigens within the immunosuppressive tumor microenvironment (TEM) (13, 14). While these studies indicate the great therapeutic potential of DC-based vaccines, curing established malignancies is rare (1, 3).

The frequent epithelial-mesenchymal transition (EMT) is an important feature of malignant mesothelioma (17). High EMT level is closely related to increased mesothelioma metastasis and poor prognosis (18, 19). The basic helix-loop-helix transcription factor TWIST1 is one of the most critical factors that induces EMT and regulates metastatic process of many solid tumors including melanoma, colon, breast, prostate, and gastric carcinomas (20-23). The role of TWIST1 remains largely unknown in regulating mesothelioma EMT and pathogenesis (25). Vaccine is a safe and easy a cost-effective way for cancer immunotherapy. Yet, its success in the clinic has been hampered by the problem of immune tolerance to tumor-associated antigen (TAA).

3. SUMMARY

Provided herewith is an effective sPD1-based TWIST1 DNA vaccine, namely sPD1-TWIST1, to break the immunotolerance to TWIST1 and elicit T cell responses directly against mesothelioma. TWIST1 expression is associated with tumorigenesis in mesothelioma patients and the protein is required for the invasion and metastasis of experimental AB1 mesothelioma. Prophylactic sPD1-TWIST1 vaccination controls both subcutaneous and metastatic mesothelioma growth. Combined sPD1-TWIST1 vaccination and CTLA-4 immune checkpoint blockade further enhances TWIST1-specific T cell responses to provide therapeutic benefits in both mesothelioma and breast cancer models. The observed antitumor therapy is dependent on the vaccine-elicited TWIST1-specific long-lasting memory CD8+ T cells that have great cytotoxicity potential and are uniquely elicited by the sPD1-TWIST1 vaccination against a highly conserved immunodominant short peptide. With the widespread expression of TWIST1 in different cancer types, sPD1-TWIST1 vaccination is useful for cancer immunotherapy.

Provided herein is a method for inducing TWIST1-specific T cell response in a subject comprising administering an effective amount of DNA vaccine comprising PD1 and TWIST1 to the subject.

In certain embodiments, the method is effective in overcoming immune tolerance to tumor-associated antigen ("TAA").

In certain embodiments, the TAA is TWIST1.

In certain embodiments, the method is effective in controlling the invasion and metastasis of cancer.

In certain embodiments, the cancer is a TWIST-1-expressing cancer.

In certain embodiments, the cancer is selected from the group consisting of mesothelioma, AB1 mesothelioma, 4T1 breast cancer, melanoma, colon cancer, prostate cancer, and gastric carcinomas.

In certain embodiments, the method further comprising administering an immune checkpoint inhibitor to the subject.

In certain embodiments, the immune checkpoint inhibitor is an anti-CTLA-4 antibody.

In certain embodiments, the effective amount of DNA vaccine construct is 100 µg-200 mg.

In certain embodiments, the vaccine is administered intramuscularly at 10 days to three-week intervals for three times.

In certain embodiments, the anti-CTLA-4 antibody is administered at a dose of 200 µg-400 mg.

In certain embodiments, the vaccine is administered intraperitoneally 24 hours after administration of the PD1-based TWIST1 vaccine and every 4 days for three times.

Provided herein is a DNA vaccine construct comprising a soluble PD1 and TWIST1.

In certain embodiments, further comprising a linker.

In certain embodiments, further comprising a tissue plasminogen activator (tPA).

Provided herein is a composition comprising a DNA vaccine construct comprising: (i) a soluble PD1; and (ii) TWIST1; and an acceptable pharmaceutical carrier.

Provided herein is a kit comprising a DNA vaccine construct comprising: (i) a soluble PD1; and (ii) TWIST1; and an acceptable pharmaceutical carrier.

4. BRIEF DESCRIPTION OF THE FIGURES

FIG. 1. Expression of TWIST1 promotes invasion and metastasis of AB1 mesothelioma. (A) TWIST1 expression in the mesothelioma cohort of TCGA (n=87) by TNM stage. Stage I/II, n=26. Stage III/IV, n=61. (B) Kaplan-Meier overall survival curve of mesothelioma patients stratified by expression level of TWIST1, with weak (n=45, TWIST1≤8.346) or strong (n=42, TWIST1>8.346) expression of TWIST1. (C) Western blot analysis of TWIST1 in different murine tumor cell lines. The functional role of TWIST1 in AB1 cells was analyzed by gene overexpression (OE) and knockout (KO) (D) Western blot analysis of TWIST1 protein. WT, wild-type AB1 cells; OE, lentiviral vector-mediated TWIST1 overexpression; KO, CRISPR/Cas9-mediated TWIST1 knockout. (E) qRT-PCR quantification of EMT related molecules including vimentin, N-cadherin and E-cadherin in wild-type, TWIST1 overexpression or knockout cells. (F) Representative wells shown for colony formation assay. (G) Matrigel cell invasion assay with representative images (upper) and quantification (lower). (H) Lung metastases after intravenous inoculation of 1×106 AB1 into BALB/c mice (n=6). Left panel, survival curve. Right panel, representative images of lungs harvested at endpoint.

Figure 2:
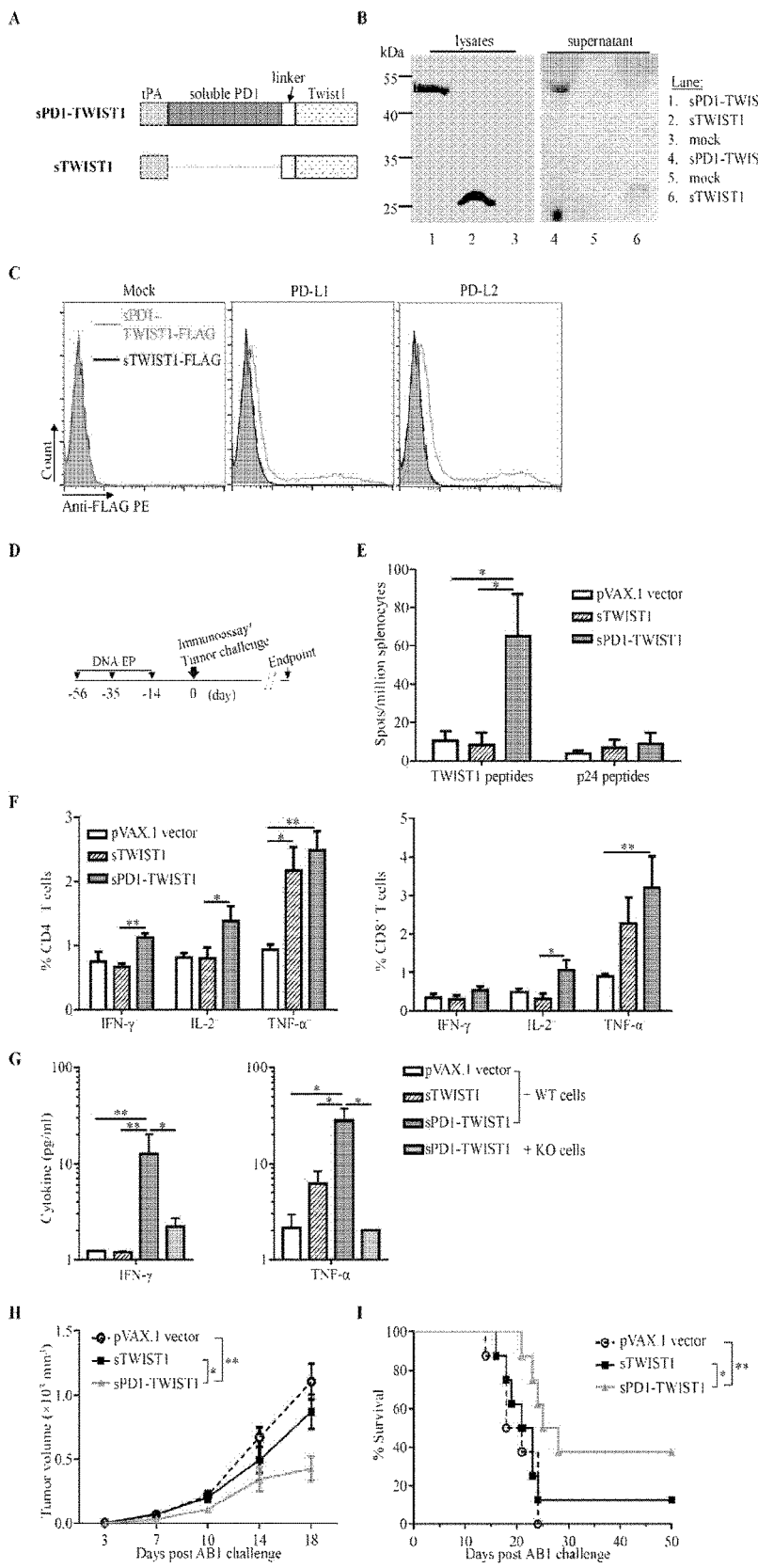

FIG. 2. PD1-based vaccination enhanced TWIST1-specific T cell responses and growth control of AB1 mesothelioma. (A) Schematic representation of TWIST1 DNA vaccine constructs. tPA, tissue plasminogen activator signal sequence. (B) Expression of TWIST1 DNA vaccine constructs after transfection in 293T cells. Cell lysates or culture supernatant of 293T cells transfected with sPD1-TWIST1, sTWIST1 or mock expression plasmids were subjected to western blot analysis using anti-TWIST1 antibody. (C) Flow cytometric analysis of binding between soluble proteins and mouse PD-L1/L2-transfected 293 cells. Transfection supernatant collected from sPD1-TWIST1-FLAG (red solid line), sTWIST1-FLAG (black dashed line) or mock (shaded region)-treated 293T cells were used to incubate 293T cells transiently transfected with mouse PD-L1 or PD-L2 expression vectors. (D) Schematic representation of treatment schedule. Groups of BALB/c mice (n=4) received three DNA/EP vaccination before sacrificed for immunoassay or challenged with 1×106 AB1 cells s.c. at 2 weeks after the last vaccination. (E) ELISpot analysis of TWIST1-specific T cell responses. (F) Intracellular staining of IFN-γ, IL-2, TNF-α-producing CD8+ (upper) and CD4+ (lower) T cells after DNA/EP vaccination. (G) Cytokine production following incubation of purified CD3+ T cells with wild-type (WT) or TWIST1 knockout (KO) AB1 cells. Tumor growth (H) and survival curves (I) of DNA/EP vaccinated mice (n=8) after s.c challenge with 1×106 AB1 cells.

Figure 3:
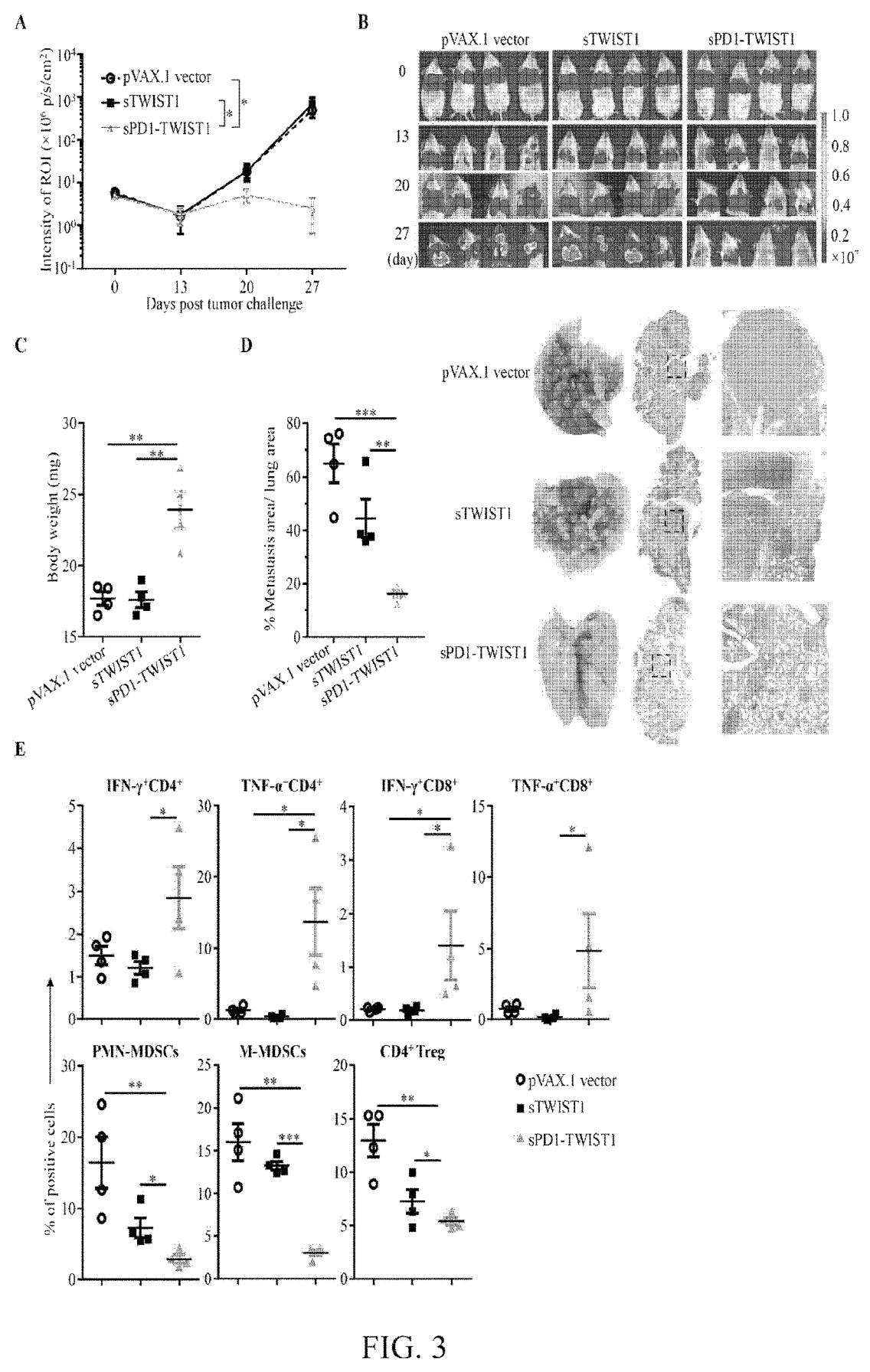

FIG. 3. sPD1-TWIST1 vaccine inhibited AB1 lung metastasis. Vaccinated BALB/c mice (n=4) received 1×106 AB1 cells 2 weeks after last vaccination and tumor growth (A) was monitored by bioluminescence and shown with representative bioluminescence images (B). On day 28, body weight of mice were measured (C) and then mice were sacrificed to collected lungs for (D) macroscopic evaluation (left) and H&E staining (right). (E) Assessment of effector function of T cell subsets (upper) and immunosuppressive cell subsets (lower) in spleen at the endpoint.

Figure 4:
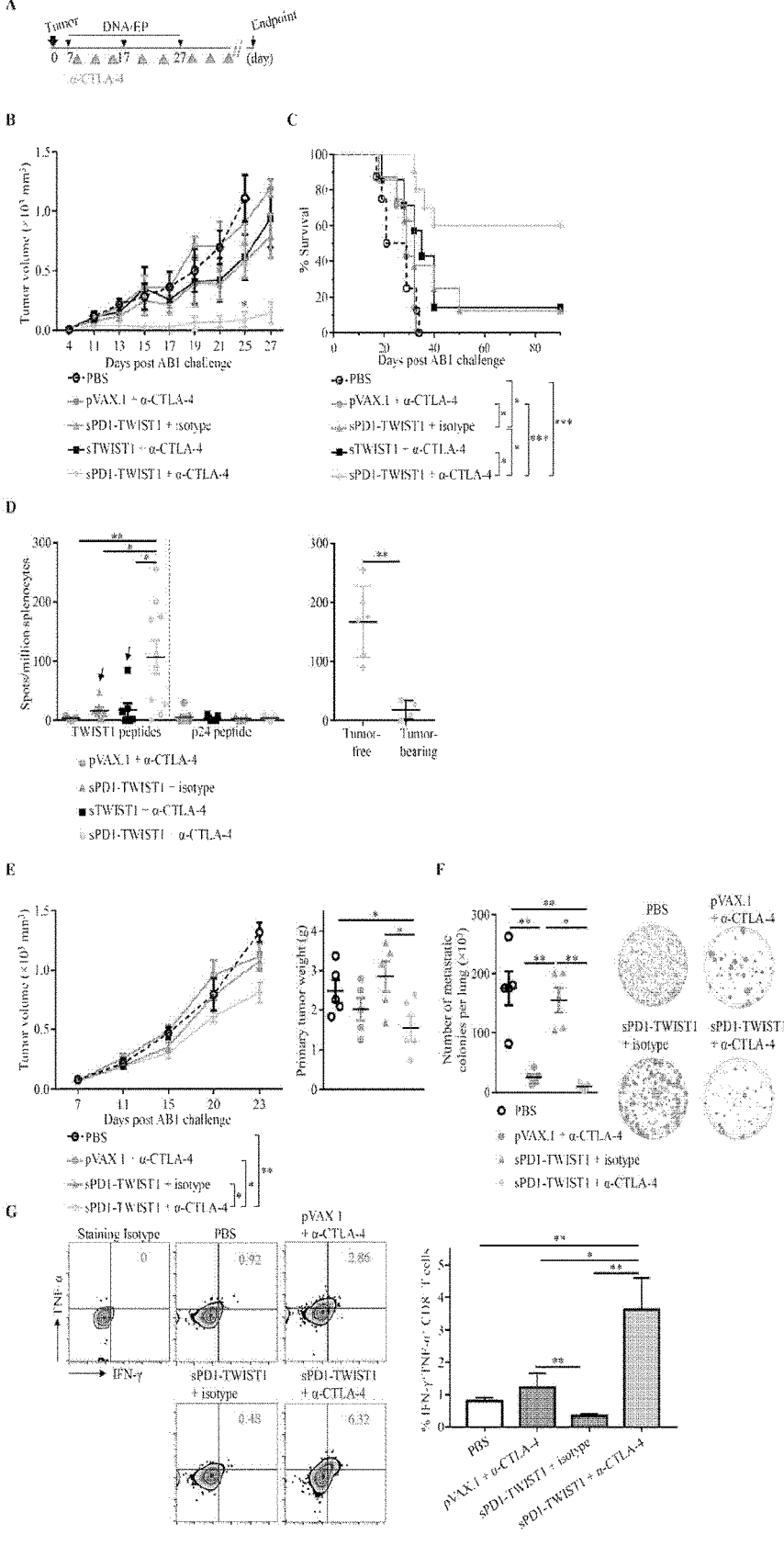

FIG. 4. Checkpoint modulation enhances the antitumor activity of sPD1-TWIST1 vaccination for curing established mesothelioma. (A) Schematic representation of therapeutic study. BALB/c mice were s.c inoculated 5×105 AB1 cells followed by sTWST1, SPD1-TWIST1 or sham vaccination, at day 7 and repeated every 10 days for three times. Anti-CTLA4 antibody at a dose of 200 μg each injection were administrated i.p at day 8 and every 4 days during the vaccination. Tumor growth measurement (B) and tumor-free survival curve (C) after therapeutic vaccination. Mice were sacrificed when tumor size was >15 mm. (D) T cell responses in all groups (left) or in combined sPD1-TWIST1 DNA/EP vaccination and CTLA-4 blockade group (right). Secreted IFN-γ was quantified by ELISpot assay after ex vivo stimulation of splenocytes with TWIST1 peptides or the control peptide ovalbumin (OVA257-264). Arrow indicated individual tumor-free mouse in that group. Groups of female BALB/c mice (n=5) were inoculated 2×105 4T1 cells in the mammary gland followed by vaccination starting at day 1 and repeated every 10 days for three times. Anti-CTLA4 antibody at a dose of 200 μg each injection were administrated i.p at day 2 and every 4 days during the vaccination. (E) 4T1 Primary tumor growth curve (left) and tumor weights (right) harvested at day 27 post 4T1 inoculation. (F) Enumeration of clonogenic metastatic cells in the lungs (left) and representative images of clonogenic colonies after 14 days incubation (right, ×200 dilution factor). (G) Representative dot plots and percentages of IFN-γ+TNF-α+ CD8+ T cells in spleens were measured at the endpoint.

Figure 5:
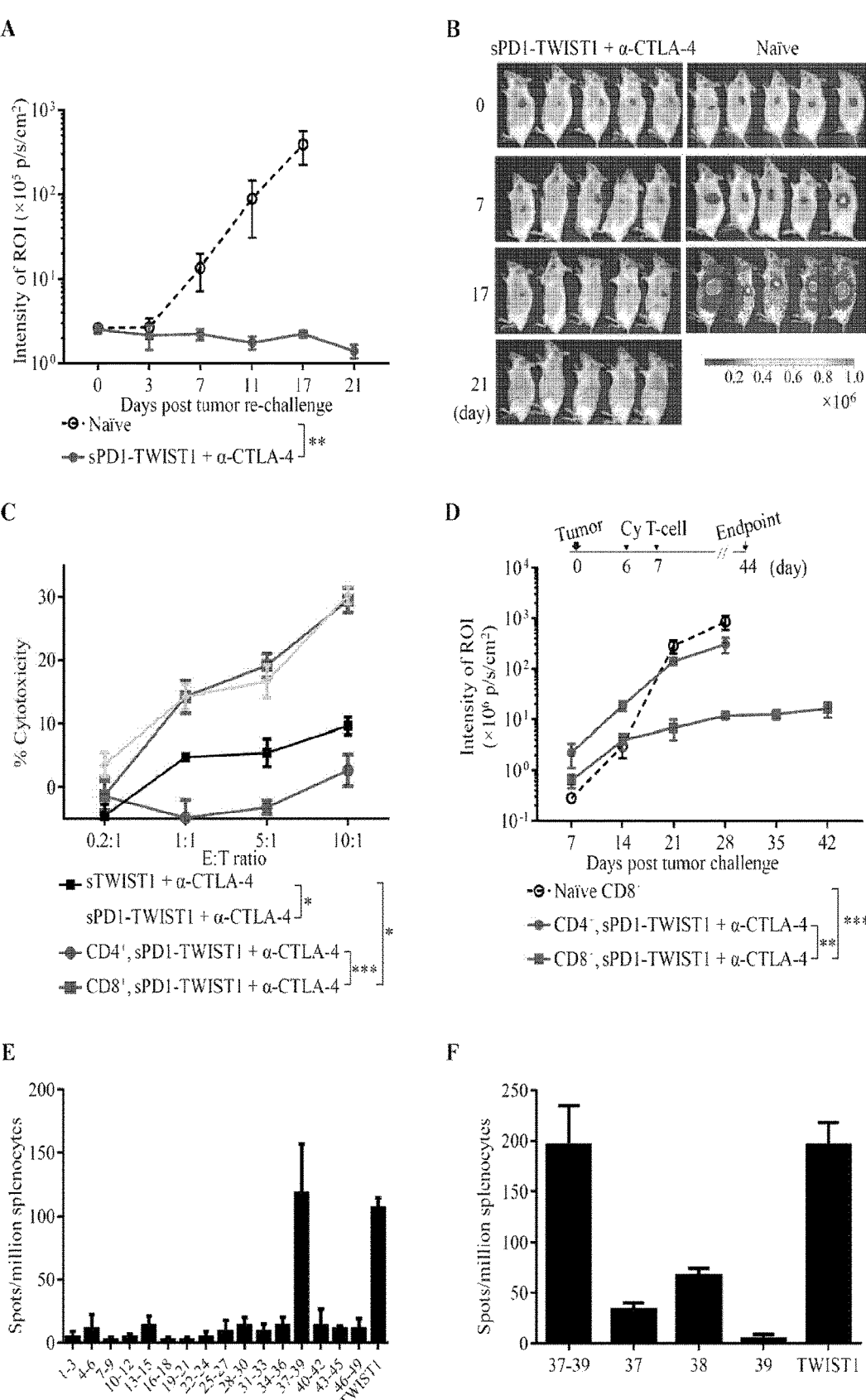

FIG. 5. Combination therapy induced durable T cell immunity responsive to an immunodominant TWIST1 epitope. 60 days after tumor ablation, protected mice (n=5) in the combined sPD1-TWIST1 and α-CTLA-4 group were re-challenged s.c. and measured for tumor growth (A) with representative bioluminescence images of AB1-Luc tumors (B). (C) Cytotoxicity assay of T cells towards AB1 cells at different effector:target (E:T) ratios. T cells were isolated from spleen of mice receiving combined sPD1-TWIST1-vaccination and α-CTLA-4 therapy after initial complete tumor rejection. (D) Schematic representation (upper) and tumor growth curve (lower) for T-cell adoptive transfer. T cells from either naïve or vaccinated/protected mice were adoptively transferred to SCID mice bearing 7-day old AB1-Luc tumors and assessed for tumor growth one day after i.p injection of 150 mg/kg cyclophosphamide (Cy). Characterization of TWIST1 immunodominant epitopes using minipools spanning the entire TWIST1 sequence (E) or peptides in minipool37-39 (F).

Figure 6:
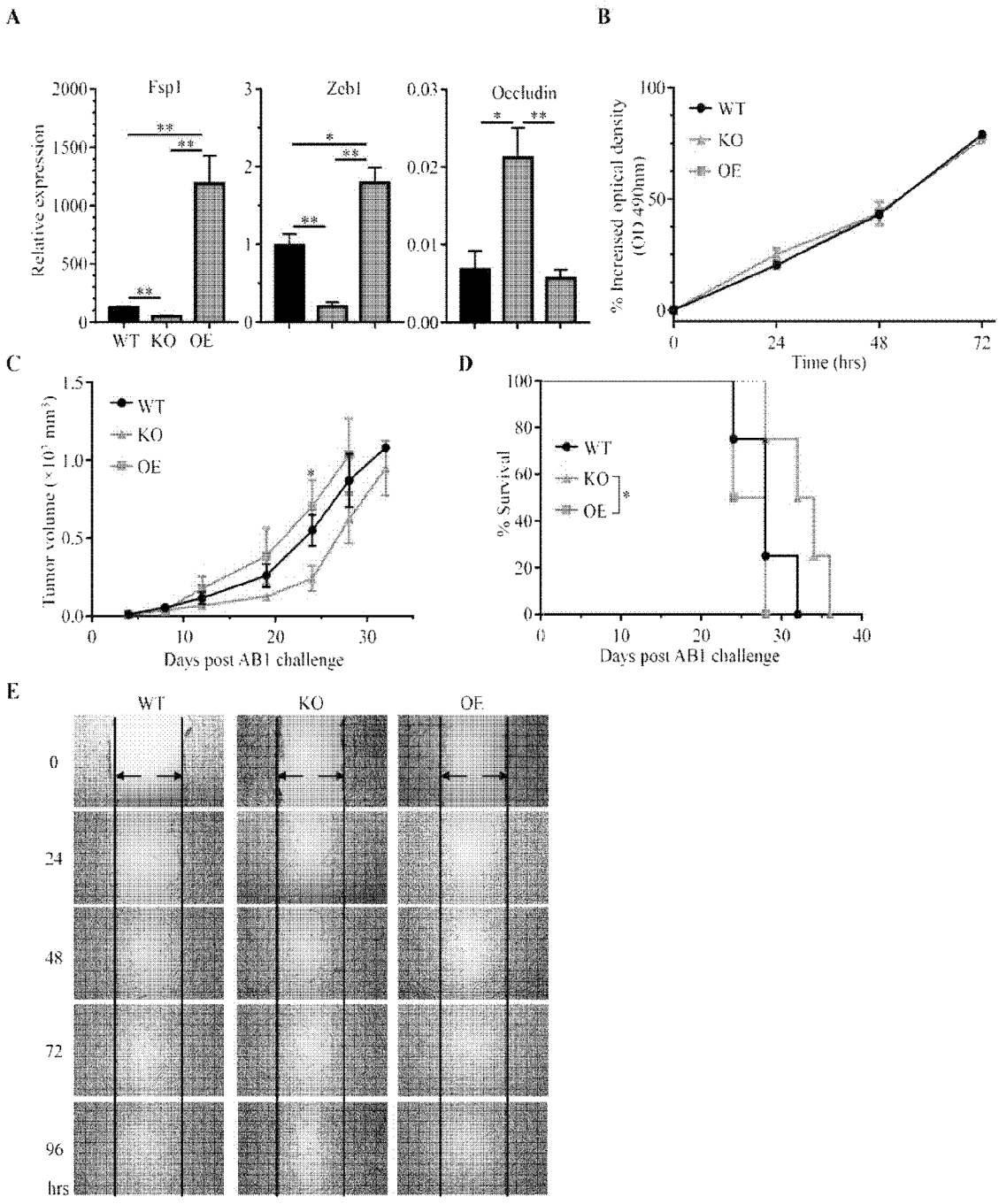

FIG. 6. Expression of TWIST1 promotes invasion and metastasis of AB1 mesothelioma. (A) qRT-PCR quantification of EMT related molecules including FSP1. ZEB1 and occludin in wild-type. TWIST1 overexpression or knockout cells. (B) In vitro proliferation of different AB1 cells with varied TWIST1 expression. Tumor growth (C) and survival curve (D) of BALB/c mice receiving s.c 1×10^6 cells. (E) Bright-field imaging in wound-healing migration assay. Cell migration into wound monitored by live-cell imaging microscopy and bright-field images were captured at the indicated times after scratching.

Figure 7:
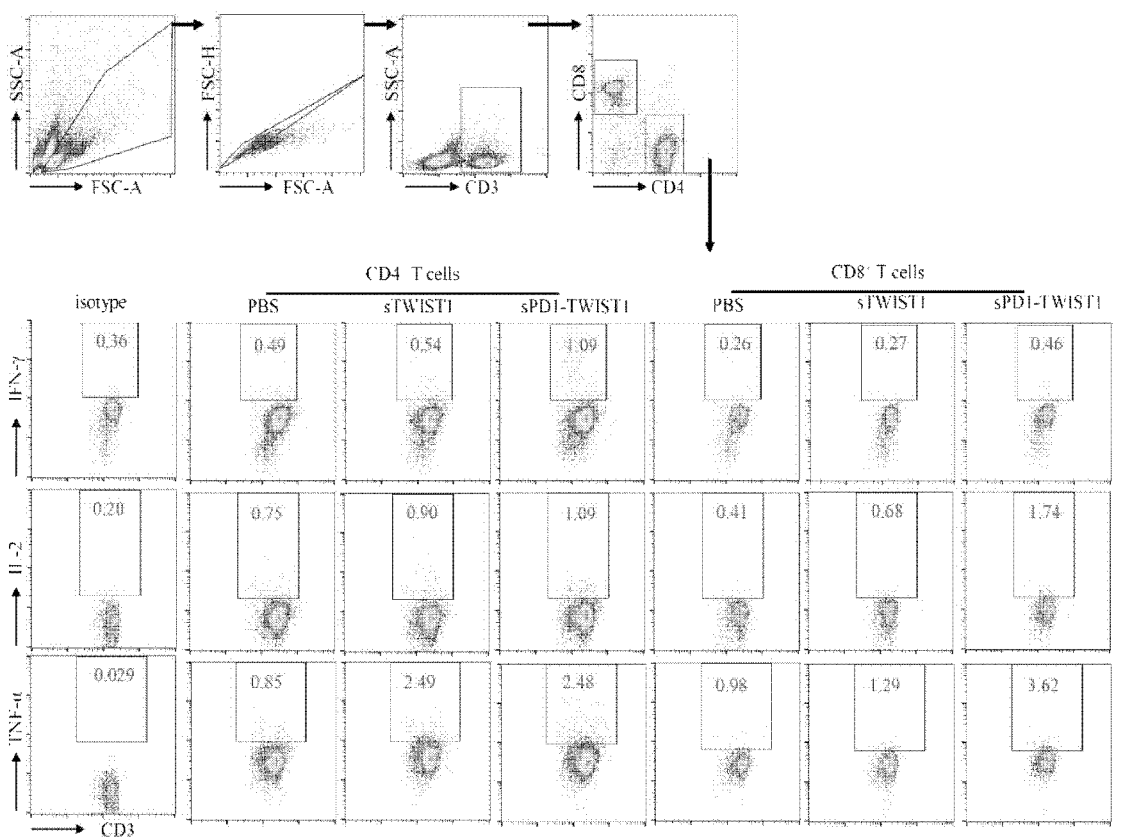

FIG. 7. PD1-based vaccination enhanced TWIST1-specific T cell responses and growth control of AB1 mesothelioma. Gating strategies for flow cytometric scatter plots showing identification of IFN-γ, IL-2, TNF-α-producing CD4+ or CD8+ T cells from splenocytes.

Figure 8:
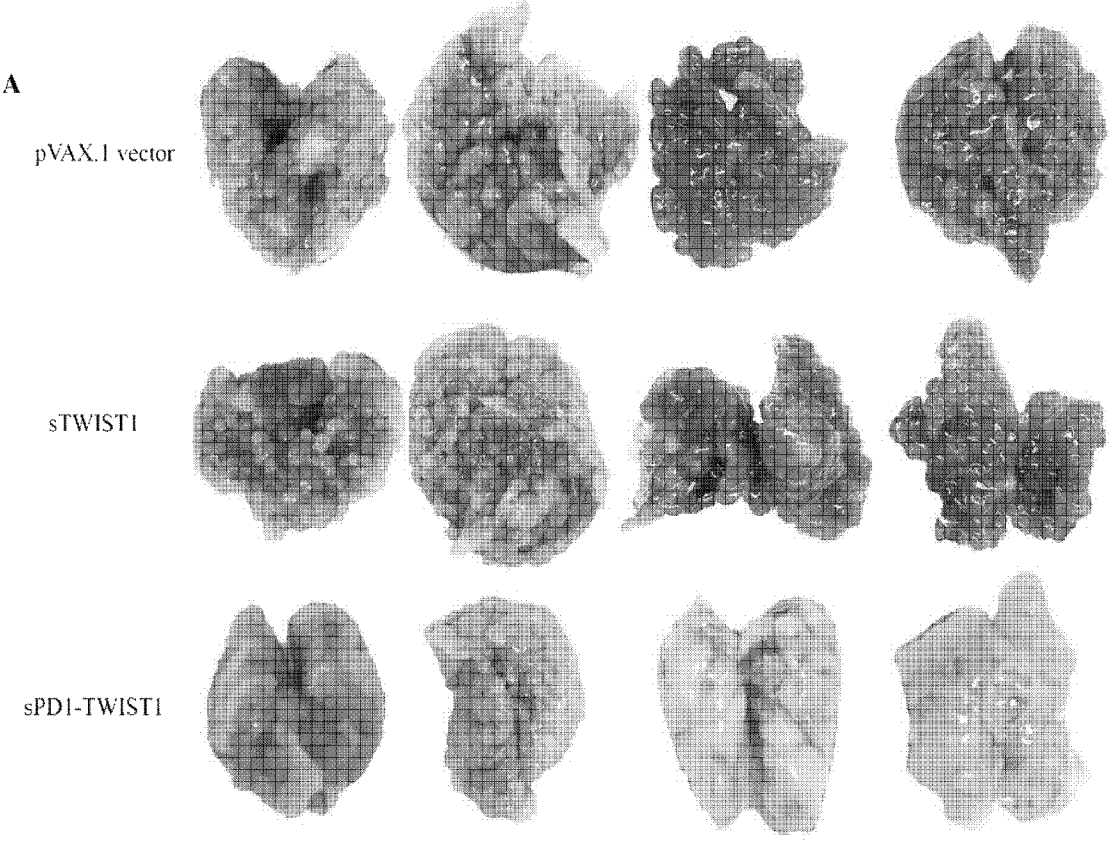
Figure 8:
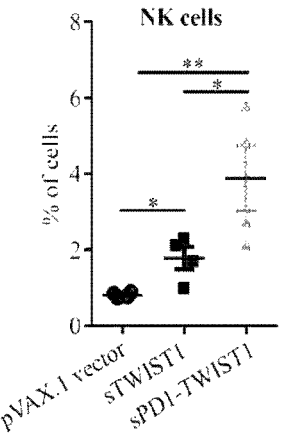

FIG. 8. sPD1-TWIST1 vaccine inhibited AB1 lung metastasis. (A) Lung images of i.v. challenged BALB/c mice at the end point. (B) Assessment of NK cells in the spleen at the endpoint.

Figure 9:
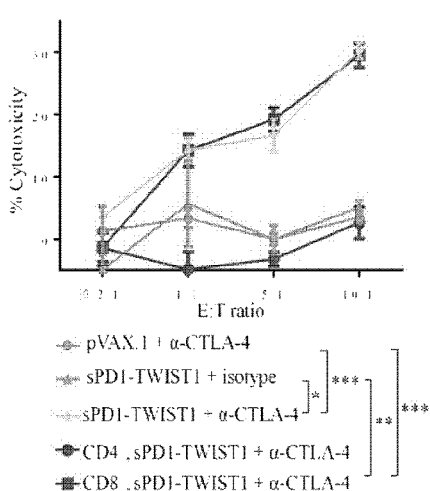
Figure 9:
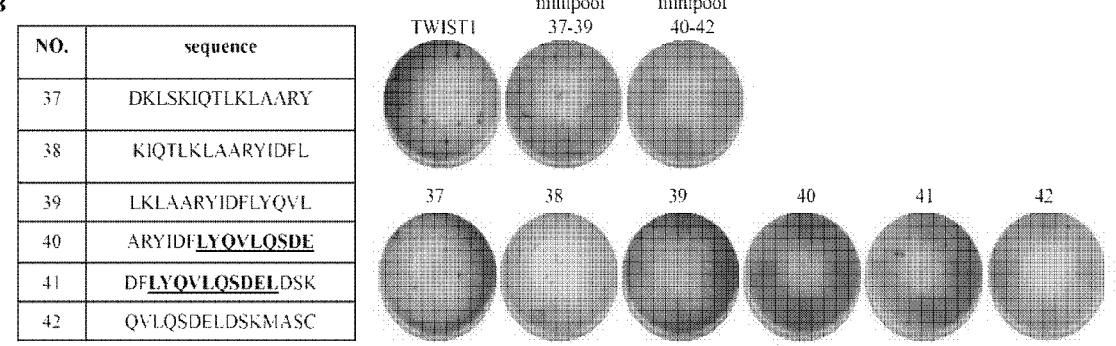

FIG. 9. Combination therapy induced durable T cell immunity responsive to an immunodominant TWIST1 epitope. (A) Cytotoxicity assay of T cells isolated from mice towards AB1 cells at different effector:target (E:T) ratios. (B) T cell responses against either TWIST1 peptides, minipool37-39, minipool40-42 or single 15-mer peptide as measured by IFN-γ ELISpot. $2\times10^5$ splenocytes from mice receiving combined sPD1-TWIST1-vaccination and α-CTLA-4 therapy after initial complete tumor rejection were used in the assay. Figure discloses SEQ ID NOS 24-29, respectively, in order of appearance.

5. DETAILED DESCRIPTION

Checkpoint immunotherapy is a major breakthrough for cancer treatment, yet its efficacy is often limited against many types of malignancies including malignant mesothelioma. Considering that the immunotherapeutic efficacy depends on immunosurveillance, an active immunization method is developed to break immune tolerance to tumor self-antigen. The limitation on TAA self-tolerance in current immunotherapy is overcome by two approaches. First, PD1-based DNA vaccination strategy is used to avoid self-tolerance for induction of TWIST1-specific anti-tumor T cell immunity. Second, a method of combined PD1-based TWIST1 vaccine and checkpoint inhibitor anti-CTLA-1 antibody significantly enhanced TWIST1-specific T cell responses, leading to immunotherapeutic cure of established mesothelioma, which had significant implication to a wide range of TWIST1-expressing cancers. TWIST1, the basic helix-loop-helix transcription factor, is associated with human mesothelioma tumorigenesis and required for the invasion and metastasis of mesothelioma in the immune competent murine AB1 model. PD1-based vaccination provided prophylactic control by inducing TWIST1-specific T cell responses against both subcutaneous and metastatic mesothelioma lethal challenges. Furthermore, while CTLA-4 blockade alone didn't show any immunotherapeutic efficacy against established mesothelioma, its combination with PD1-based vaccination resulted in 60% complete remission. Mechanistically, these functional T cells recognized a novel highly conserved immunodominant TWIST1 epitope, exhibited cytotoxic activity and long-lasting memory, and led to durable tumor regression and survival benefit against established AB1 mesothelioma and 4T1 breast cancer. PD1-based vaccination controls mesothelioma by breaking immune tolerance to the tumor self-antigen TWIST1. Provided herein is a PD1-based vaccination to enhance immunotherapy against a wide range of TWIST1-expressing tumors.

Results

TWIST1 expression correlated with mesothelioma progression and promoted invasion and metastasis of AB1 mesothelioma. We initially investigated the effect of TWIST1 expression in human mesothelioma by comparing its expression level between different stages of 87 patients from the mesothelioma cohort (MESO) of The Cancer Genome Atlas (TCGA). Higher TWIST1 expression was found in patients with advanced-stage mesothelioma (TNM III and IV) as compared with early-stage tumors (TNM I or II) (FIG. 1A). In addition, when the patients were stratified into two groups based on the TWIST1 expression in their tumors, patients with strong TWIST1 expression showed a significantly reduced overall survival (FIG. 1B), suggesting an association of TWIST1 expression with mesothelioma tumorigenesis.

We next examined the expression of TWIST1 protein in two mesothelioma cell lines, AB1 and AE17, as well as in the 4T1 breast cancer cell line. Consistent with previous findings (26), TWIST1 was detected in 4T1 cells (FIG. 1C). Moreover, we found that both mesothelioma cell lines also expressed TWIST1 proteins with the highest expression level detected in AB1 cells. To explore the role of TWIST1 expression in AB1 mesothelioma development, we constructed AB1 cells in which TWIST1 expression was manipulated by either lentiviral vector-mediated overexpression or CRISPR/Cas9-mediated knockout (KO), respectively (FIG. 1D). Using real-time qPCR, we found that overexpression of TWIST1 induced the expression of mesenchymal markers including vimentin, N-cadherin, fibroblast specific protein 1 (FSP-1) and zinc finger E-box-binding homeobox 1 (ZEB1), as well as suppression of E-cadherin and occludin expression (FIG. 1E and FIG. 6A). This result suggested that TWIST1 may coordinate with other EMT transcriptional factors to promote EMT and metastasis of mesothelioma. Although TWIST1 overexpression or silencing did not alter the short-term proliferation of AB1 cells in vitro (FIG. 6B), colony formation efficiency of AB1 cells closely correlated with TWIST1 expression (FIG. 1F). Specifically, overexpression cells showed enhanced clonogenic activity while KO cells showed reduced activity. In line with their in vitro clonogenic activity, subcutaneous overexpression tumors exhibited comparably accelerated growth rate and significantly shortened survival time compared to subcutaneous KO tumors in syngeneic BALB/c mice (FIG. 6C-D). We next sought to determine whether TWIST1 expression affects invasion and metastasis of AB1 mesothelioma. KO of TWIST1 expression profoundly decreased migration of AB1 cells, whereas its overexpression promoted it, in both Matrigel cell invasion assay (FIG. 1G) and wound-healing migration assay (FIG. 6E). To further verify the role of TWIST1 in driving mesothelioma metastasis, we established an in vivo metastasis model by intravenous (i.v.) injection of AB1 cells via the tail vein of BALB/c immunocompetent mice, which resulted in forming metastatic foci in the whole lungs and humane euthanasia of all treated animals was required within 30 days due to clinical outcomes (FIG. 1H). Using this model, we found that, compared to wild-type (WT) cells, TWIST1 overexpression enhanced metastatic activity of AB1 cells while KO significantly suppressed their ability to metastasize to the lungs and prolonged tumor-free survival of animals. Overall, these findings support the notion that TWIST1 is an important transcription factor underlying mesothelioma invasion, metastasis and tumor progression, suggesting that TWIST1 may serve as a therapeutic target to arrest cancer growth and metastasis.

PD1-based vaccination enhanced TWIST1-specific T cell responses and growth control of AB1 mesothelioma. In order to determine whether sPD1-based fusion DNA vaccine would enhance TWIST1-specific anti-mesothelioma immunity, we first generated DNA vaccine construct encoding a fusion protein linking sPD1 with TWIST1 (SPD1-TWIST1) to compare with a conventional sTWIST1 DNA vaccine (FIG. 2A). Expression of encoding TWIST1 proteins from these two constructs was confirm by western blot analysis (FIG. 2B). Importantly, while both TWIST1 proteins could be secreted as soluble forms, only sPD1-TWIST1 interacted with PD-L1/L2-expressing cells (FIG. 2B-C), suggesting that sPD1-based TWIST1 vaccine may improve adaptive T cell immunity by targeting TWIST1 antigen to DCs as previously indicated (11, 28). To test this, we sought to determine whether sPD1-TWIST1 could enhance TWIST1-specific immune responses in vivo in BALB/c mice. Briefly, 100 μg DNA plasmid of either sPD1-TWIST1 or sTWIST1 were injected intramuscularly (i.m) via EP at three-week intervals for three times, as we have previously established (11, 28). Two weeks after the last vaccination, all mice were sacrificed and blood and spleen specimens were collected for immune response analysis (FIG. 2D). We found that sPD1-TWIST1 vaccination significantly elevated TWIST1-specific T cell responses compared to sTWIST1 vaccination (FIG. 2E). Moreover, sPD1-TWIST1-vaccinated mice had substantially higher frequencies of IFN-γ- and TNF-α-expressing CD4+ T cells, as well as TNF-α-expressing CD8+ T cells after ex vivo stimulation with the TWIST1 peptide pool (FIG. 2F and FIG. 7), indicating that the sPD1-based vaccine breaks tolerance to the TWIST1 self-antigen. Importantly, when compared to controls, CD3+ T cells of sPD1-TWIST1-vaccinated mice released significantly higher amounts of IFN-γ and TNF-α when co-cultured in vitro with WT AB1 cells, but not with TWIST1 KO cells (FIG. 2G), thus demonstrating the specificity of vaccine-elicited T cells in recognizing TWIST1-expressing tumor cells. In order to evaluate the ability of TWIST1 vaccination to control tumor growth in vivo, a lethal dose of 1×106 WT AB1 cells were inoculated subcutaneously (s.c.) into vaccinated mice two weeks after the third vaccination (FIG. 2D). We found that the sPD1-TWIST1 vaccine significantly inhibited AB1 mesothelioma growth compared to the sTWIST1 or mock vaccine (FIG. 2H). Furthermore, only the sPD1-TWIST1-vaccinated mice substantially prolonged the survival time of AB1-challenged mice, leading to 37.5% tumor-free survival (FIG. 2I). Taken together, our results supported the notion that the sPD1-TWIST1 vaccine is useful to break TWIST1 immunotolerance for generating protective immunity against mesothelioma.

sPD1-TWIST1 vaccine inhibited AB1 lung metastasis. Since the expression of TWIST1 was responsible for mesothelioma metastatic activity, we next sought to study the activity of TWIST1 vaccines in inhibiting metastasis of AB1 mesothelioma cells. Using the same metastasis model described above, vaccine-immunized mice were injected i.v. with WT AB1 cells stably transduced with firefly luciferase (AB1-Luc) to induce pulmonary metastasis and pulmonary tumor growth was monitored by bioluminescence imaging. Compared to mock vaccination, the non-targeting sTWIST1 DNA vaccine failed to show any anti-mesothelioma activity (FIG. 3A-B). Significant reduction of lung metastasis was only found in sPD1-TWIST1 vaccinated mice. At the end point at 28 days post AB1 injection, mice in sTWIST1-vaccinated and mock-treated groups showed significantly reduced body weight (FIG. 3C). Importantly, in line with in vivo imaging results, sPD1-TWIST1-vaccinated mice had significantly reduced metastasized nodules on the lung surface (FIG. 8A) and fewer metastatic area in the lungs (FIG. 3D), suggesting a strong impact of sPD1-TWIST1 in inhibiting metastasis of AB1 mesothelioma. It has been reported that the establishment of an immunosuppressive environment is associated with tumor immune escape and mesothelioma development (11, 29, 30). To illustrate the importance of vaccine-elicited T cell immunity in overcoming the mesothelioma-associated immunosuppressive environment in this metastasis model, we analyzed the T cell functionality as well as frequencies of various immunosuppressive cells ex vivo at the experimental end point. We found that sPD1-TWIST1-vaccinated mice had significantly higher levels of IFN-γ and TNF-α-producing CD4+ and CD8+ T cells (FIG. 3E), as well as NK cells (FIG. 8B) compared to controls. Furthermore, frequencies of immunosuppressive cells, including the polymorphonuclear and monocytic myeloid-derived suppressor cells (MDSC) subsets and CD4+ regulatory T cells (Treg), were significantly lower in SPD1-TWIST1-vaccinated mice than the sTWIST-1- or mock-vaccinated mice (FIG. 3F). Collectively, these results demonstrated that sPD1-TWIST1 vaccination inhibited metastasis of AB1 mesothelioma and reduced tumor-associated immunosuppression.

Checkpoint modulation enhances the antitumor activity of sPD1-TWIST1 vaccination for curing established mesothelioma. Given the success of antibody-mediated immune checkpoint blockade in relieving regulation of endogenous antitumor T cell responses in tumor-burdened hosts, we asked whether anti-mesothelioma responses generated by the sPD1-TWIST1 vaccine can benefit from checkpoint blockade with anti-CTLA-4 (α-CTLA-4) antibody. We hypothesized that the α-CTLA-4 antibody may enhance the antitumor activity of sPD1-TWIST1 vaccination (31). To test this hypothesis, we initially studied the antitumor efficacy against established AB1 mesothelioma. Mice were first inoculated s.c. with the lethal dose of 5×105 AB1 cells followed by sTWIST1, SPD1-TWIST1 or sham vaccination three times in 10-day intervals, starting at 7 days post tumor inoculation when the solid tumors were palpable (FIG. 4A). At the same time, α-CTLA-4 antibody at a dose of 200 μg each injection were administrated intraperitoneally (i.p.) at day-8 and every 4 days during the vaccination. We found that the a-CTLA-4 monotherapy did not show any antitumor activity against established AB1 mesothelioma and all the mice needed to be euthanized within 40 days due to their clinical outcomes (FIG. 4B-C). SPD1-TWIST1 vaccination monotherapy displayed modest anti-mesothelioma activity with slow tumor growth and resulted in tumor regression in 1/6 mice. Notably, combined therapy of sPD1-TWIST1 vaccination and α-CTLA-4 caused retarded tumor growth and there was a significant reduction in tumor volume compared to both α-CTLA-4 monotherapy and PBS-treated groups, as measured at 25 days post tumor inoculation (p=0.0224, compared to α-CTLA-4 alone; p=0.0386, compared to PBS). The combined therapy of PD1-based vaccine with α-CTLA-4 treatment also led to tumor eradication in 6/10 of the mice while sTWIST1 and α-CTLA-4 combined therapy failed to show significant enhancement on animal survival with only 1/7 tumor-free survival at the endpoint (FIG. 4B-C). This result demonstrated the critical role of sPD1-TWIST1 vaccination in eliciting efficacious antitumor responses. We then determined the TWIST1-specific T cell response in these mice and found that splenocytes from the sPD1-TWIST1 vaccination and α-CTLA-4 combined therapy elicited more TWIST1-specific T cells whereas neither sTWIST1 vaccination and α-CTLA-4 combined therapy nor monotherapies can do so (FIG. 4D). Notably, mice with tumor eradication elicited potent IFN-γ T cell responses than tumor-bearing mice, demonstrating the involvement of vaccine-elicited T cell responses in clearing established AB1 mesothelioma. In a separate model, previous studies have demonstrated principally the role of TWIST1 in 4T1 breast cancer metastasis and TWIST1 vaccination for breast cancer immunotherapy (26, 27). We found that the combined therapy of sPD1-TWIST1 and a-CTLA-4 reduced tumor growth and size of primary 4T1 mammary tumors and had a more potent antitumor effect against 4T1 lung metastases (FIG. 4E-F), which was accompanied by markedly increased IFN-γ+TNF-α+CD8+ T cells in vivo (FIG. 4G). Taken together, these results demonstrated that administration of checkpoint modulator α-CTLA-4 significantly enhanced antitumor activity elicited by sPD1-TWIST1 vaccination, inducing regression of established AB1 mesothelioma as well as growth inhibition of mammary and metastatic 4T1 breast cancer.

Combination therapy induced durable T cell immunity responsive to an immunodominant TWIST1 peptide. We next sought to study the durability of the antitumor response induced by combined sPD1-TWIST1 and α-CTLA-4. In another group of mice which had eliminated AB1 mesothelioma after receiving the combined therapy of sPD1-TWIST1 and a-CTLA-4, an additional higher dose of 1×106 AB1-Luc cells were re-challenged s.c. on their contralateral flank >90 days after the initial complete tumor rejection. Complete rejection of AB1-Luc mesothelioma was observed 21 days later in these mice, while all naïve mice succumbed to AB1-Luc challenge (FIG. 5A-B), suggesting the induction of prolonged memory responses. In order to dissect the types of T cells responsible for mesothelioma elimination, in vitro cytotoxicity assay was performed with purified splenic T cells from sPD1-TWIST1-vaccinated mice after initial complete tumor rejection. Consistent with IFN-γ responses described above, CD3+ T cells from mice receiving combined sPD1-TWIST1 and α-CTLA-4 showed enhanced in vitro cytotoxic activity in comparison to either the sTWIST1 combined therapy (FIG. 5C) or monotherapies (FIG. 9A). More importantly, the killing of target cells was performed by CD8+ T cells, but not CD4+ T cells (FIG. 5C). In addition, adoptive transfer of these cytotoxic CD8+ T cells resulted in retarded tumor growth and prolonged survival in SCID mice bearing AB1-Luc tumors (FIG. 5D), demonstrating the critical role of the combined therapy in inducing efficacious anti-mesothelioma CTLs. We next characterized the TWIST1 amino acid sequences recognized by T cells induced by combined sPD1-TWIST1 and α-CTLA-4. Ex vivo isolated splenocytes were firstly screened in an ELISpot assay with minipools containing three 15-mers spanning the entire TWIST1 protein. And specific reactivity was mostly found against the minipool 37-39 (DKLSKIQTLK-LAARYIDFLYQVL (SEQ ID NO: 1)) (FIG. 5E and FIG. 9B). In contrast, no response was found against minipool 40-42

```
                                   (SEQ ID NO: 2)
         (ARYIDFLYQVLQSDELDSKMASC),
``` which contains the previously reported epitope LYQVLQS-DEL (SEQ ID NO: 3) (26, 32). We then tested the individual single 15-mers in the two minipools and found that peptides 37 and 38 showed strong activity than peptide 39, suggesting that peptide 37-38 (DKLSKIQTLKLAARYIDFL (SEQ ID NO: 4)) contains the immunodominant epitope in BALB/c mice (FIG. 5F and FIG. 9B). Notably, this sequence is highly conserved across different host species. Therefore, these data demonstrated that combined therapy elicited vaccine-specific and durable antitumor CD8+CTLs responsive to an immunodominant short epitope within TWIST1 protein.

Discussion

Elucidation of novel and potential therapeutic targets for treating malignant mesothelioma remains an urgent need in the absence of effective treatments for this aggressive tumor type. Previous studies have described the use of yeast and poxviral vectors to deliver TWIST1 as an immunotherapeutic approach to elicit antigen-specific T cell responses to control breast and prostate cancers in mouse models (26, 27, 33). In comparison, this study is the first, to our knowledge, to demonstrate the induction of TWIST1-specific T cells with a DNA vaccine in an immune competent mesothelioma cancer model. Our results demonstrate that sPD1-TWIST1 vaccination has potential as a therapeutic intervention for mesothelioma immunotherapy because it provides tumor suppression in both subcutaneous and metastatic mesothelioma challenges that are dependent on TWIST1-specific T cell responses. Importantly, we show that sPD1-TWIST1 vaccination in combination with CTLA-4 immune checkpoint blockade further activates and enhances TWIST1-specific T cells with better cytotoxic activity and long-last memory in an immunosuppressive TME, leading to durable tumor regression and survival benefit against the established AB1 mesothelioma and 4T1 breast cancer in mice. Finally, we found that efficacious T cells recognize a highly immunodominant short peptide that is highly conserved across murine and human TWIST1 sequence, thus providing rationale for further optimization of a human PD1-TWIST1 vaccine to maximize its efficacy and minimize potential side-effects.

Our study shows that TWIST1 is required for mesothelioma invasion and metastasis. In numerous tumor models, cancer cells were shown to remain dependent on TWIST1 to sustain proliferation or to promote metastatic spread through EMT induction (20, 21, 23). However, only two previous publications, one in abstract form, have reported the possible association between upregulated TWIST1 expression and poor prognosis in mesothelioma (24, 25). The role of elevated TWIST1 expression in mesothelioma remains unexplored. Here, we report the link between TWIST1 expression and clinical stages of mesothelioma patients. By knockout and overexpression approaches, we further demonstrate that TWIST1 promotes expression of EMT-related molecules and positively regulates mesothelioma cell invasion in vitro and metastasis in vivo. The promotion of invasion by TWIST1 was detected in two different invasion assays. To study the metastatic potential mediated by TWIST1 expression in vivo, we established an experimental metastasis model by intravenous injection of AB1 cells, which results in lung metastasis and rapid death of animals. We found that silencing TWIST1 nearly abolished the metastatic ability of AB1 mesothelioma while its overexpression did not further enhance metastasis significantly, implying that maintenance of extremely high TWIST1 expression may not be necessary for mesothelioma when invasion and intravasation are accomplished (22, 23). Interestingly, though to a lesser extent, TWIST1 promotes clonogenic potential and subcutaneous tumor growth of AB1 mesothelioma. In keeping with this, previous studies also found that TWIST1 interferes with the p53 tumor suppressor pathway to provide survival advantage for varieties of malignant cells (20, 21). Overall, inhibiting TWIST1 arrests mesothelioma growth and metastasis. We, therefore, support that TWIST1 could serve as a potential antigen for mesothelioma vaccine.

The sPD1-TWIST1 vaccine is immunogenic for eliciting T cell responses. Targeting TAAs, which are self-proteins abnormally expressed by cancer cells, is a common strategy of tumor vaccines. However, this approach faces the problem of thymic deletion of high-affinity T cells, leaving an attenuated low-avidity repertoire. Nevertheless, therapeutic vaccination of differentiation antigens (e.g. tyrosinase-related protein 2, TRP2) or cancer testis antigens (e.g. prostate acid phosphatase, PAP) has been shown to bypass the thymic tolerance and induce tumor regression in cancer patients (14, 34-36). TWIST1 is expressed mostly in murine testis or human placenta, making it a possible cancer antigen candidate for therapeutic vaccines (26, 37). Indeed, two TWIST1-based vaccines, delivered by either yeast or pox-viral vector, have demonstrated the ability to elicit TWIST1-specific CD8+ and CD4+ T cell immune responses without any apparent toxic effect (26, 27, 33). However, both vac-cination strategies showed limited T cell activation and therapeutic efficacy, suggesting the need for improving vaccine immunogenicity. Here, we adopted two approaches to enhance TWIST1-specific T cell responses and achieve the most effective tumor clearance. One is to employ the sPD1-based vaccination and the other is to combine this vaccine with immune checkpoint inhibitor.

The present study demonstrates that breaking tolerance to TWIST1 with DNA vaccine requires the fusion of TWIST1 antigen to the sPD1. It has been previously reported that sPD1-based vaccination potentiated HIV-1 p24-specific CD8+ T cell responses by enhancing antigen binding and uptake by DCs via the PD1/PD-L interaction (28). In addi-tion, sPD1-p24 vaccination as a monotherapy elicited potent effector CD8+ T cells to prevent and cure malignant meso-thelioma expressing the p24 xenoantigen (11). Adaption of such strategy to TWIST1 successfully resulted in the induc-tion of TWIST1-specific CD8+ and CD4+ T cells, which was not achieved by the conventional sTWIST1 vaccination. While the vaccine-encoded sPD1-TWIST1 retains the abil-ity to secrete extracellularly for binding to PD-L1/L2, the use of EP for vaccine administration would induce localized inflammation in vivo to promote DC recruitment (28), which might also contribute to the enhancement of vaccine immu-nogenicity detected. The vaccine-elicited T cells were reac-tive towards AB1 mesothelioma via recognizing TWIST1 expression, leading to rejection of implanted subcutaneous AB1 tumors and reduction of lung metastasis. Notably, increased vaccine-elicited IFN-γ- and TNF-α-producing CD4+/CD8+ T cells is accompanied by suppression of immunosuppressive network such as MDSCs and Foxp3+ CD4+Treg. All of these attributes may contribute to the generation of anti-TWIST1 immune responses and to the improved prophylactic effects that we observed with sPD1-TWIST1 vaccination.

The combined sPD1-TWIST1 and α-CTLA-4 antibody treatment works synergistically to enhance TWIST1-spe-cific T cell responses and immunotherapeutic efficacy. Until now, the induction of antitumor T cells through vaccination has been met with less clinical success, potentially because the induced immune responses are not potent or broad enough to generate a desirable clinical outcome, or the acquisition of immune checkpoint molecules by effector T cells in the TME render them progressively exhausted and unable to exert effector functions (13, 38, 39). In addition, CTLA-4 and PD1 blockades as monotherapy only work in a restricted number of patients and their clinical benefits are most effective in the presence of pre-existing tumor-specific T cell responses (40). Therefore, recent studies have been exploring combination strategies in order to enhance the overall efficacy of these novel treatment strategies. Combi-nations of cancer vaccines and immune checkpoint modu-lation have shown promising results in both pre-clinical models and cancer patients (31, 41-43). Accordingly, since PD1 blockades would disrupt the targeting of sPD1-TWIST1 protein with PD-L interaction for antigen delivery (28), we hypothesized that sPD1-TWIST1 vaccination induced antitumor T cell responses can be optimized when combined with α-CTLA-4 antibody instead. We found that neither α-CTLA-4 antibody nor sPD1-TWIST1 vaccination as a monotherapy can induce mesothelioma regression. Their combined immunotherapy, however, induces effective and durable CD8+ CTLs for the clearance of mesothelioma. We believe that this dual treatment works through multiple mechanisms of action. On one hand, sPD1-based DC tar-geting is essential because the non-targeting vaccine, even in the combined immunotherapy setting, fails to induce T cell responses, thus highlighting the unique advantage of sPD1-based vaccination strategy in priming T cell immunity. One the other hand, α-CTLA-4 antibody is essential to revert immunosuppression on T cell priming which otherwise is nearly abolished in sPD1-TWIST1 vaccination mono-therapy. Nevertheless, activation of CD8+ CTLs is critical to the success of the combined immunotherapy observed in both AB1 mesothelioma and 4T1 breast cancer models, although the detailed mechanisms by which they mediate antitumor activity have yet to be elucidated. Together, our results reveal the main limitations of the use of either vaccination or CTLA-4 blockade as monotherapy against malignant mesothelioma. More importantly, we demonstrate the superiority of the combined sPD1-based vaccination and α-CTLA-4 antibody immunotherapy for promoting antitu-mor immunotherapeutic efficacy.

Efficacious T cells elicited from combined sPD1-TWIST1 vaccination and α-CTLA-4 therapy recognize a highly immunodominant short peptide within TWIST1 antigen, which has not been reported before this study. Previously, the TWIST1 epitope LYQVLQSDEL (SEQ ID NO: 3) was identified to specifically activate murine CTLs against the 4T1 breast cancer, which was published as an abstract form (44). This epitope was used in following studies to detect TWIST1-specific T cell responses by assessing IFN-γ pro-duction in ex vivo culture supernatant after long-term stimu-lation of T cells, suggesting it's probably a weak inducer of T cell responses (26, 32, 33). In contrast, our results dem-onstrate that T cells responsive to a short peptide of minipool 37-39 other than the epitope LYQVLQSDEL (SEQ ID NO: 3) are dominantly present in the mice cured of AB1 meso-thelioma. It is possible that the specificity observed is probably dependent on PD1-based vaccination approach and tumor type. Nevertheless, our findings provide rationale for further optimization of PD1-based TWIST1 vaccine design.

In summary, immunization with a sPD1-based DNA vaccine encoding TWIST1 induces TWIST1-specific T cell responses, inhibits metastasis, and controls mesothelioma growth. Rational combination of sPD1-TWIST1 vaccination and CTLA-4 immune checkpoint modulation promotes TWIST1-specific T cell-mediated tumor rejection. With broad range of expression across various solid tumor types, this preclinical study will serve as a foundation for clinical studies targeting human TWIST1 antigen in the future.

6. EXAMPLES

Methods

Mice. All mice were maintained according to standard operational procedures at HKU Laboratory Animal Unit (LAU) and all procedures were approved by the Committee on the Use of Live Animals in Teaching and Research (CULATR) of HKU (license #4249-17). 6-8 week-old female BALB/c and SCID mice were used.

Cell lines and culture conditions. AB1 cell line, purchased from European Collection of Cell Cultures, and 4T1 cell line, a kind grift from Prof. Jian-Dong Huang (School of Biomedical Science, HKU), were maintained in complete Roswell Park Memorial Institute-1640 medium (RPMI, Gibco; supplemented with 10% FBS, 2 mM L-glutamine and antibiotics). To generate TWIST1 KO tumor cells, HEK293T cells were transfected with the lentiviral expression vector pLentiCRISPR containing Cas9-single guide RNA targeting TWIST1 (TWIST1 sgRNA, 5'-TTGCTCAGGCTGTCGTCGGC-3' (SEQ ID NO: 5)) along with pCMV-VSV-G and psPAX2 plasmids, kind gifts from Dr. Kin-Hang Kok (Department of Microbiology, HKU). To generate TWIST1 overexpression tumor cells, Twist1 gene was cloned into pCDH vector (System Biosciences) and used for transfection of HEK293T cells, together with pPACKH1 lentiviral packaging system (System Biosciences). Virus from supernatants of these transfections were used to transduce AB1 cells followed by puromycin selection. TWIST1 overexpression, KO and luciferase-expressing cell lines (AB1-Luc) were maintained in complete RPMI supplemented with 1 μg/ml puromycin (Thermo Scientific). T cells and splenocytes were cultured in complete RPMI supplemented with 50 M 2-mercaptoethanol (Sigma).

Antibodies. The following antibodies were used for western blotting: anti-TWIST1 (clone Twist2C1a, Abcam), anti-β-actin (clone AC-15, Abcam) and anti-GAPDH (clone EPR16891, Abcam). The following antibody were purchased from eBioscience and used for flow cytometry: anti-CD11b (clone M1/70), anti-Ly6C (clone HK1.4), anti-Ly6G (clone 1A8-Ly6g), anti-CD3 (clone 17A2), anti-CD4 (clone GK1.5), anti-CD8 (clone 53-6.7), anti-PD1 (clone J43). The following antibody were purchased from BioLegend and used for flow cytometry: anti-CD25 (clone 3C7), anti-Foxp3 (clone 150D), anti-CD49b (HMα2), anti-PD-L1 (clone 10F.9G2), anti-PD-L2 (clone TY25), anti-IFN-γ (clone XMG1.2), anti-TNF-α (clone MP6-XT22), anti-IL-2 (clone JES6-5H4). Cell surface and intracellular immunostaining were performed as previously described (11). Flow cytometric data analysis was performed using the FlowJo software (Tree Star, v10). Anti-CTLA4 antibody used in in vivo studies was purchased from BioXcell (clone 9D9).

Tumor models. Tumor cells were harvested and single cell suspensions of 5×105 cells in 100 μl PBS were injected s.c into right hind flank (for AB1 model) or into the second mammary gland (for 4T1 model) of BALB/c mice. Tumor volumes were measured by caliper (Tumor volume=½(length×width2)). Luciferase-expressing tumors were measured with IVIS spectrum (PerkinElmer) and presented as photons/s/cm2/sr within regions of interest (ROI) using Living Image software (version 4.0, PerkinElmer), as previously described(11, 45). In the AB1 experimental metastasis model, 1×106 AB1 cells were injected into the tail vein of BALB/c mice and the colonization of AB1 cells in the lung were determined by noninvasive bioluminescence imaging and H&E staining at the endpoint. AB1-Luc re-challenge was performed 60 days after primary tumor ablation on the opposite flank of animals. In the 4T1 spontaneous metastasis model, metastasis of 4T1 tumor cells into the lung are examined with a standard colonogenic assay at the endpoint(46). Specimens were fixed in Zinc Formalin Fixative (sigma) and then embedded in paraffin blocks for following H&E staining. Metastatic area was defined as the percentage of lung area occupied by metastatic tumor, measured by ImageJ.

Quantitative reverse transcriptase-PCR. Total cell RNA was extracted with RNeasy Kit (Qiagen) and cDNA generated by SuperScript III First-Strand Kit (Thermo Scientific).

Then PCR was performed using the following primers with PrimeStar HS DNA Polymerase (Takara):

```
Twist1,
                                (SEQ ID NO: 6)
        5'-AGCTACGCCTTCTCCGTCTG-3', (SEQ ID NO: 7)
        5'-CTCCTTCTCTGGAAACAATGACA-3';

Vimentin,
                                (SEQ ID NO: 8)
        5'-TGACCTCTCTGAGGCTGCCAACC-3', (SEQ ID NO: 9)
        5'-TTCCATCTCACGCATCTGGCGCTC-3';

N-cadherin,
                                (SEQ ID NO: 10)
        5'-AAAGAGCGCCAAGCCAAGCAGC-3', (SEQ ID NO: 11)
        5'-TGCGGATCGGACTGGGTACTGT G-3';

E-cadherin,
                                (SEQ ID NO: 12)
        5'-ACACCGATG GTGAGGGTACACAGG-3', (SEQ ID NO: 13)
        5'-GCCGCCACACACAGC ATAGTCTC-3';

Fsp1,
                                (SEQ ID NO: 14)
        5'-CCTGTCCTGCATTGCCATGAT-3', (SEQ ID NO: 15)
        5'-CCCACTGGCAAACTACA CCC-3';

Zeb1,
                                (SEQ ID NO: 16)
        5'-GATTCCCCAAGTGGCATATACA-3', (SEQ ID NO: 17)
        5'-TGGAGACTCCTTCTGAGCTA GTG-3';

Occludin,
                                (SEQ ID NO: 18)
        5'-TGCTAAGGCAGTTTTGGCTAAGTCT-3', (SEQ ID NO: 19)
        5'-AAAAACAGTGGTGG GGAACATG-3';

actin,
                                (SEQ ID NO: 20)
        5'-GGCATGGGTCAGAAGGATT-3', (SEQ ID NO: 21)
        5'-GGGGTGTTGAAGGTCT CAAA-3';

Gapdh,
                                (SEQ ID NO: 22)
        5'-GGTCCTCAGTGTAGCCCAAG-3', (SEQ ID NO: 23)
        5'-AATGTGTCCGTCGTGGATCT-3'.
```

In vitro tumor cell-based assays. AB1 cells at a density of 0.5×10⁴ cells each well were plated into 96-well plate in complete RPMI medium for proliferation assay, with MTS cell viability assay (Promega) performed at 0, 24, 48 and 72 hours according to the manufacturer's instructions. Colony formation assay was performed in 6-well plate with an initial cell density of 500 AB1 cells each well in complete RPMI medium and colonies were stained with crystal violet (0.5 w/v) 9 days later, according to a standard protocol (47). For monolayer wound healing assay, 1×106 cells were plated into 6-well plate one day before scratching by a plastic tip (1 mm). After cell washing to remove debris, cells were cultured in complete RPMI medium to monitor wound healing over time. For cell invasion assay, AB1 cells were starved overnight in serum-free RPMI medium. 30 μl thawed Matrigel (BD Biosciences) was used to coat each invasion chamber (Transwell, BD Biosciences) equipped with an 8 μm pore size Micropore filter. The chambers were then incubated at 37° C. for 30 min and rinsed gently with serum-free RPMI. In the meantime, AB1 cells were harvested after trypsinization, washed once with serum-free RPMI medium. Then 250 μl AB1 cells at a density of 1×106 cells/ml in serum-free RPMI was added to the upper chamber. 500 μl RPMI was added to the bottom chamber with 10% FBS as chemoattractant. After incubation at 37° C. for 24 h, the Matrigel on the filter was removed with a cotton swap. After crystal violet staining, the membrane was washed several times with PBS before taking images. Then cell stain was dissolved with extraction buffer for 30 min at room temperature and absorbance was read with a microplate reader at 560 nm.

Ex vivo cell preparation. Splenocytes were isolated as previously described (11, 45). Tumors were cut into pieces and digested with 1 mg/ml collagenase IV (Sigma) and 0.5 U/ml DNase I (Roche) for 1.5-2.0 hours at 37° C. Cells were passed through a 70 μm strainer and then subjected to 40%/80% Percoll gradient (Sigma). Leukocytes at the interphase were recovered after centrifugation at ×800 g 20 min. T cells, including CD3+, CD4+ and CD8+ T cells, were isolated by Untouched T Cell Isolation Kit (Miltenyi Biotech).

ELISpot, cytokine production assay and T cell cytotoxicity assay. IFN-γ-producing T cells in isolated splenocytes was assessed by ELISpot assay (11, 45). A mouse TWIST1 peptide library of 49 peptides generated as 15-mers overlapping by 11 amino acids was synthesized by GL Biochem (Shanghai). Cytokine concentrations in co-culture supernatant were measured by LEGENDplex T Helper Cytokine Panel (BioLegend). Cytotoxic effect of purified T cells against AB1 cells was determined using NonRadioactive Cytotoxicity Assay (Promega) according to the manufacturer's instructions.

Statistical Analyses. All data are presented as mean±s.e.m. Information on the study outline, sample size, and statistical analysis is shown in the main text, figures, and figure legends. Significance of mean differences was determined using non-parametric Mann-Whitney U-tests or Wilcoxon matched-pairs tests for unpaired and paired analysis, respectively, to compare data sets. Two-way ANOVA was used to compare mouse tumor volume data among different groups. Survival data was plotted on Kaplan-Meier survival curve and the log-rank (Mantel-Cox) test was performed to analyze differences in GraphPad Prism 7 software. In all statistical analyses. *p<0.05. p<0.01 and *p<0.001.

REFERENCES

1. Scherpereel A, Wallyn F, Albelda S M, Munck C. Novel therapies for malignant pleural mesothelioma. Lancet Oncol. 2018; 19(3):e161-e72.
2. Baldini E H, Richards W G, Gill R R, Goodman B M, Winfrey O K, Eisen H M, et al. Updated patterns of failure after multimodality therapy for malignant pleural mesothelioma. J Thorac Cardiovasc Surg. 2015; 149(5):1374-81.
3. Yap T A, Aerts J G, Popat S, Fennell D A. Novel insights into mesothelioma biology and implications for therapy. Nat Rev Cancer. 2017; 17(8):475-88.
4. Dozier J, Zheng H, Adusumilli P S. Immunotherapy for malignant pleural mesothelioma: current status and future directions. Transl Lung Cancer Res. 2017; 6(3):315-24.
5. Kindler H L. The Challenge of Defining Treatment Standards for a Rare Disease: Malignant Peritoneal Mesothelioma. J Oncol Pract. 2016; 12(10):936-7.
6. Guazzelli A, Bakker E, Krstic-Demonacos M, Lisanti M P, Sotgia F, Mutti L. Anti-CTLA-4 therapy for malignant mesothelioma. Immunotherapy. 2017; 9(3):273-80.
7. Alley E W, Lopez J, Santoro A, Morosky A, Saraf S, Piperdi B, et al. Clinical safety and activity of pembrolizumab in patients with malignant pleural mesothelioma (KEYNOTE-028): preliminary results from a non-randomised, open-label, phase 1b trial. Lancet Oncol. 2017; 18(5):623-30.
8. Schunselaar L M, Quispel-Janssen J M, Neefjes J J, Baas P. A catalogue of treatment and technologies for malignant pleural mesothelioma. Expert Rev Anticancer Ther. 2016; 16(4):455-63.
9. Zhang L, Conejo-Garcia J R, Katsaros D, Gimotty P A, Massobrio M, Regnani G, et al. Intratumoral T cells, recurrence, and survival in epithelial ovarian cancer. N Engl J Med. 2003; 348(3):203-13.
10. Galon J. Costes A, Sanchez-Cabo F. Kirilovsky A, Mlecnik B. Lagorce-Pages C, et al. Type, density, and location of immune cells within human colorectal tumors predict clinical outcome. Science. 2006; 313(5795):1960-4.
11. Tan Z, Zhou J, Cheung A K, Yu Z, Cheung K W, Liang J, et al. Vaccine-elicited CD8+ T cells cure mesothelioma by overcoming tumor-induced immunosuppressive environment. Cancer Res. 2014; 74(21):6010-21.
12. Yamada N, Oizumi S, Kikuchi E, Shinagawa N, Konishi-Sakakibara J, Ishimine A, et al. CD8+ tumor-infiltrating lymphocytes predict favorable prognosis in malignant pleural mesothelioma after resection. Cancer Immunol Immunother. 2010; 59(10):1543-9.
13. Hollingsworth R E, Jansen K. Turning the corner on therapeutic cancer vaccines. NPJ Vaccines. 2019; 4:7.
14. Kantoff P W, Higano C S, Shore N D, Berger E R, Small E J, Penson D F, et al. Sipuleucel-T immunotherapy for castration-resistant prostate cancer. N Engl J Med. 2010; 363(5):411-22.
15. Cornelissen R, Hegmans J P, Maat A P, Kaijen-Lambers M E, Bezemer K, Hendriks R W, et al. Extended Tumor Control after Dendritic Cell Vaccination with Low-Dose Cyclophosphamide as Adjuvant Treatment in Patients with Malignant Pleural Mesothelioma. Am J Respir Crit Care Med. 2016; 193(9):1023-31.
16. Aerts J, Cornelissen R, Van Der Leest C, Hegmans J, Bezemer K, Kaijen-Lambers M, et al. Autologous Dendritic Cells Loaded with Allogeneic Tumor Cell Lysate (Pheralys (R)) in Patients with Mesothelioma: Final Results of a Phase I Study. J Thorac Oncol. 2017; 12(1):S295-S.
17. Fassina A, Cappellesso R, Guzzardo V, Dalla Via L, Piccolo S. Ventura L, et al. Epithelial-mesenchymal transition in malignant mesothelioma. Mod Pathol. 2012; 25(1):86-99.
18. Hmeljak J, Sanchez-Vega F, Hoadley K A, Shih J, Stewart C, Heiman D, et al. Integrative Molecular Characterization of Malignant Pleural Mesothelioma. Cancer Discov. 2018; 8(12):1548-65.
19. de Reynies A, Jaurand M C, Renier A, Couchy G, Hysi I, Elarouci N, et al. Molecular classification of malignant pleural mesothelioma: identification of a poor prognosis subgroup linked to the epithelial-to-mesenchymal transition. Clin Cancer Res. 2014; 20(5):1323-34.

20. Puisieux A, Valsesia-Wittmann S, Ansieau S. A twist for survival and cancer progression. Br J Cancer. 2006; 94(1):13-7.

21. Ansieau S, Bastid J, Doreau A, Morel A P, Bouchet B P, Thomas C, et al. Induction of EMT by twist proteins as a collateral effect of tumor-promoting inactivation of premature senescence. Cancer Cell. 2008; 14(1):79-89.

22. Yang J, Mani S A, Donaher J L, Ramaswamy S, Itzykson R A, Come C, et al. Twist, a master regulator of morphogenesis, plays an essential role in tumor metastasis. Cell. 2004; 117(7):927-39.

23. Weiss M B, Abel E V. Mayberry M M, Basile K J, Berger A C, Aplin A E. TWIST1 is an ERK1/2 effector that promotes invasion and regulates MMP-1 expression in human melanoma cells. Cancer Res. 2012; 72(24):6382-92.

24. Romagnoli S, Fasoli E, Vaira V, Falleni M, Pellegrini C, Catania A, et al. Identification of potential therapeutic targets in malignant mesothelioma using cell-cycle gene expression analysis. Am J Pathol. 2009; 174(3):762-70.

25. Suraokar M B, Kim D, Zhang Y, Diao L X, Riguelme E, Behrens C, et al. Exploring the role of Twist1 in the pathogenesis of malignant pleural mesothelioma (MPM). Cancer Research. 2012; 72.

26. Ardiani A, Gameiro S R, Palena C, Hamilton D H, Kwilas A, King T H, et al. Vaccine-mediated immunotherapy directed against a transcription factor driving the metastatic process. Cancer Res. 2014; 74(7):1945-57.

27. Malamas A S, Hammond S A, Schlom J, Hodge J W. Combination therapy with an OX40L fusion protein and a vaccine targeting the transcription factor twist inhibits metastasis in a murine model of breast cancer. Oncotarget. 2017; 8(53):90825-41.

28. Zhou J, Cheung A K, Tan Z, Wang H, Yu W. Du Y, et al. PD1-based DNA vaccine amplifies HIV-1 GAG-specific CD8+ T cells in mice. J Clin Invest. 2013; 123(6):2629-42.

29. Lindau D, Gielen P, Kroesen M, Wesseling P, Adema G J. The immunosuppressive tumour network: myeloid-derived suppressor cells, regulatory T cells and natural killer T cells. Immunology. 2013; 138(2):105-15.

30. Yu Z, Tan Z, Lee B K, Tang J, Wu X. Cheung K W, et al. Antigen spreading-induced CD8+ T cells confer protection against the lethal challenge of wild-type malignant mesothelioma by eliminating myeloid-derived suppressor cells. Oncotarget. 2015; 6(32):32426-38.

31. Hailemichael Y, Woods A, Fu T, He Q. Nielsen M C, Hasan F, et al. Cancer vaccine formulation dictates synergy with CTLA-4 and PD-L1 checkpoint blockade therapy. J Clin Invest. 2018; 128(4):1338-54.

32. Vanpouille-Box C, Diamond J M, Pilones K A, Zavadil J, Babb J S, Formenti S C, et al. TGFbeta Is a Master Regulator of Radiation Therapy-Induced Antitumor Immunity. Cancer Res. 2015; 75(11):2232-42.

33. Kwilas A R, Ardiani A, Dirmeier U, Wottawah C. Schlom J, Hodge J W. A poxviral-based cancer vaccine the transcription factor twist inhibits primary tumor growth and metastases in a model of metastatic breast cancer and improves survival in a spontaneous prostate cancer model. Oncotarget. 2015; 6(29):28194-210.

34. Boon T, van der Bruggen P. Human tumor antigens recognized by T lymphocytes. J Exp Med. 1996; 183(3):725-9.

35. Patel P M, Ottensmeier C H, Mulatero C, Lorigan P. Plummer R, Pandha H, et al. Targeting gp100 and TRP-2 with a DNA vaccine: Incorporating T cell epitopes with a human IgG1 antibody induces potent T cell responses that are associated with favourable clinical outcome in a phase I/II trial. Oncoimmunology. 2018; 7(6):e1433516.

36. Sahin U, Derhovanessian E, Miller M, Kloke B P, Simon P. Lower M, et al. Personalized RNA mutanome vaccines mobilize poly-specific therapeutic immunity against cancer. Nature. 2017; 547(7662):222-6.

37. Qin Q. Xu Y. He T, Qin C, Xu J. Normal and disease-related biological functions of Twist1 and underlying molecular mechanisms. Cell Res. 2012; 22(1):90-106.

38. Schreiber R D, Old L J, Smyth M J. Cancer immuno-editing: integrating immunity's roles in cancer suppression and promotion. Science. 2011; 331(6024):1565-70.

39. Sharma P. Hu-Lieskovan S, Wargo J A, Ribas A. Primary, Adaptive, and Acquired Resistance to Cancer Immunotherapy. Cell. 2017; 168(4):707-23.

40. Wei S C, Duffy C R, Allison J P. Fundamental Mechanisms of Immune Checkpoint Blockade Therapy. Cancer Discov. 2018; 8(9):1069-86.

41. Field C S, Hunn M K, Ferguson P M, Ruedl C, Ancelet L R, Hermans I F. Blocking CTLA-4 while priming with a whole cell vaccine reshapes the oligoclonal T cell infiltrate and eradicates tumors in an orthotopic glioma model. Oncoimmunology. 2017; 7(1):e1376154.

42. Wilgenhof S, Corthals J, Heirman C, van Baren N, Lucas S, Kvistborg P, et al. Phase II Study of Autologous Monocyte-Derived mRNA Electroporated Dendritic Cells (TriMixDC-MEL) Plus Ipilimumab in Patients With Pre-treated Advanced Melanoma. J Clin Oncol. 2016; 34(12): 1330-8.

43. Ribas A, Comin-Anduix B. Chmielowski B, Jalil J, de la Rocha P. McCannel T A, et al. Dendritic cell vaccination combined with CTLA4 blockade in patients with metastatic melanoma. Clin Cancer Res. 2009; 15(19):6267-76.

44. Wang B, Santori F, Demaria S. A metastasis regulator is a target of CD8+ anti-tumor T cells. Proc Amer Assoc Cancer Res. 2006; 47: Abstract #2241.

45. Tan Z, Liu L, Chiu M S, Cheung K W. Yan C W, Yu Z, et al. Virotherapy-recruited PMN-MDSC infiltration of mesothelioma blocks antitumor CTL by IL-10-mediated dendritic cell suppression. Oncoimmunology. 2019; 8(1): e1518672.

46. Yang S, Zhang J J, Huang X Y. Mouse models for tumor metastasis. Methods Mol Biol. 2012; 928:221-8.

47. Franken N A, Rodermond H M, Stap J, Haveman J, van Bree C. Clonogenic assay of cells in vitro. Nat Protoc. 2006; 1(5):2315-9.

The foregoing description of the specific embodiments will so fully reveal the general nature of the disclosure that others can, by applying knowledge within the skill of the relevant art(s) (including the contents of the documents cited and incorporated by reference herein), readily modify and/or adapt for various applications such specific embodiments, without undue experimentation, without departing from the general concept of the present disclosure. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present disclosure have been described above, it should be understood that they have been presented by way of examples, and not limitation. It would be apparent to one skilled in the relevant art(s) that various changes in form and detail could be made therein without departing from the spirit and scope of the disclosure. Thus, the present disclosure should not be limited by any of the above-described exemplary embodiments but should be defined only in accordance with the following claims and their equivalents.

All references cited herein are incorporated herein by reference in their entirety and for all purposes to the same extent as if each individual publication or patent or patent application was specifically and individually indicated to be incorporated by reference in its entirety for all purposes.

The invention claimed is:

1. A DNA vaccine construct encoding a fusion protein comprising soluble PD1 linked with TWIST1, and wherein the fusion protein comprises a TWIST1 peptide consisting of the amino acid sequence of SEQ ID NO: 4.

2. The DNA vaccine construct of claim 1 further comprising a linker.

3. The DNA vaccine construct of claim 2 further comprising a tissue plasminogen activator (tPA).

4. A composition comprising a DNA vaccine construct encoding a fusion protein comprising: (i) a soluble PD1; and (ii) TWIST1, wherein the soluble PD1 is linked to the TWIST1; and an acceptable pharmaceutical carrier, and wherein the fusion protein comprises a TWIST1 peptide consisting of the amino acid sequence of SEQ ID NO: 4.

5. A kit comprising a DNA vaccine construct encoding a fusion protein comprising (i) a soluble PD1; and (ii) TWIST1, wherein the soluble PD1 is linked to the TWIST1; and an acceptable pharmaceutical carrier, and wherein the fusion protein comprises a TWIST1 peptide consisting of the amino acid sequence of SEQ ID NO: 4.

6. A method for inducing TWIST1-specific T cell response in a subject having TWIST1 overexpressed cancer, comprising administering to the subject an effective amount of a DNA vaccine comprising a DNA construct encoding a fusion protein comprising soluble PD1 linked with TWIST1, wherein the fusion protein comprises a TWIST1 peptide consisting of the amino acid sequence of SEQ ID NO: 4.

7. The method of claim 6 wherein the method is effective in controlling the invasion and metastasis of the TWIST1 overexpressed cancer.

8. The method of claim 6 wherein the TWIST1 overexpressed cancer is selected from the group consisting of mesothelioma, AB1 mesothelioma, 4T1 breast cancer, melanoma, colon cancer, prostate cancer, and gastric carcinomas.

9. The method of claim 6 further comprising administering an immune checkpoint inhibitor to the subject.

10. The method of claim 9 wherein the immune checkpoint inhibitor is an anti-CTLA-4 antibody.

11. The method of claim 6 wherein the effective amount of the DNA vaccine construct is 100 μg-200 mg.

12. The method of claim 11 wherein the DNA vaccine is administered intramuscularly at 10 days to three-week intervals for three times.

13. The method of claim 10 wherein the anti-CTLA-4 antibody is administered at a dose of 200 μg-400 mg.

14. The method of claim 13 wherein the anti-CTLA-4 antibody is administered intraperitoneally 24 hours after administration of the DNA vaccine and every 4 days for three times.

*     *     *     *     *